United States Patent
Melamed

(10) Patent No.: US 9,244,021 B2
(45) Date of Patent: Jan. 26, 2016

(54) APPARATUS FOR MONITORING REVERSE OSMOSIS MEMBRANE CONDITION

(71) Applicant: VAYYAR IMAGING LTD., Yehud (IL)

(72) Inventor: Raviv Melamed, Nes Ziona (IL)

(73) Assignee: VAYYAR IMAGING LTD., Yehud (IL)

( * ) Notice: Subject to any disclaimer, the term of this patent is extended or adjusted under 35 U.S.C. 154(b) by 230 days.

(21) Appl. No.: 14/040,503

(22) Filed: Sep. 27, 2013

(65) Prior Publication Data

US 2014/0176157 A1 Jun. 26, 2014

Related U.S. Application Data

(60) Provisional application No. 61/706,174, filed on Sep. 27, 2012.

(51) Int. Cl.
*G01N 22/00* (2006.01)
*B01D 61/12* (2006.01)

(52) U.S. Cl.
CPC ............... *G01N 22/00* (2013.01); *B01D 61/12* (2013.01)

(58) Field of Classification Search
CPC .. G06F 19/3418; B01D 9/005; B01D 9/0063; B01D 2311/24; B01D 2313/18; B01D 61/025; B01D 61/12; G01F 3/20; Y02E 60/366; G01N 22/00; G01N 2800/52; G01N 29/0654; C02F 11/001; C02F 1/32; C02F 1/441; C02F 1/444

See application file for complete search history.

(56) References Cited

U.S. PATENT DOCUMENTS

| | | | | |
|---|---|---|---|---|
| 4,235,723 A | * | 11/1980 | Bartlett, Jr. | 210/321.83 |
| 4,409,849 A | * | 10/1983 | Roos | 73/863.82 |
| 7,481,917 B2 | * | 1/2009 | Ikeyama et al. | 210/85 |
| 7,584,061 B2 | * | 9/2009 | Wilf et al. | 702/35 |
| 8,393,167 B2 | * | 3/2013 | Krause et al. | 62/125 |

* cited by examiner

*Primary Examiner* — Vinh Nguyen
(74) *Attorney, Agent, or Firm* — Mark Cohen; Pearl Cohen Zedek Latzer Baratz

(57) ABSTRACT

A microwave imaging sensor is disclosed for continuously monitoring the condition and status of an in situ reverse osmosis membrane that forms a semi-permeable barrier between a region of water containing a dissolved salt and a region of water which is intended to be substantially free of the dissolved salt. A device according to embodiments of the invention can be used to monitor the condition of the membrane, i.e., the ability of the membrane to filter water by reverse osmosis; and to detect failures in the membrane such as leaking saline water into the output stream. The results of the monitoring can be used to determine in real time whether or not the membrane should be replaced.

2 Claims, 3 Drawing Sheets

APPARATUS FOR MONITORING REVERSE OSMOSIS MEMBRANE CONDITION

CROSS REFERENCE TO RELATED APPLICATIONS

This application claims benefit of U.S. Provisional Patent Application Ser. No. 61/706,174, filed Sep. 27, 2012, the disclosure of which is hereby incorporated by reference and the priority of which is hereby claimed pursuant to 37 CFR 1.78(a) (4) and (5)(i).

BACKGROUND

Reverse osmosis (RO) membranes are often used in large quantities to desalinate water on a commercial scale. Because many membranes are typically connected in parallel to a common output, it is hard to localize a performance degradation and/or failure to individual membranes. Therefore, to maintain output water quality at an acceptable level, membranes are typically replaced according to a time-based replacement schedule. A time-based replacement policy is undesirable for a variety of reasons:

- The frequency of membrane replacement is not necessarily optimal. Under certain conditions, the membranes may be replaced too frequently, thereby reducing cost-effectiveness. Under other conditions, the membranes may not be replaced frequently enough, thereby reducing water output quality.
- Not all membranes necessarily degrade at the same rate. Two membranes installed at the same time do not necessarily have to be replaced at the same time.
- A membrane not only degrades in time, but is also subject to random failure that can result in the leakage of saline water into the output stream. Random failures of this sort cannot be effectively handled according to a time-based replacement schedule.

It would therefore be beneficial to have a means of detecting the real-time in situ condition of RO membranes on an individual basis, so that the membranes can be replaced on an as-needed basis in response to performance degradation and/or failure. This goal is met by the present invention.

SUMMARY

Embodiments of the invention provide a microwave imaging sensor for continuously monitoring the condition and status of an in situ RO membrane that forms a semi-permeable barrier between a region of water containing a dissolved salt ("saline water") and a region of water which is intended to be substantially free of the dissolved salt. In certain non-limiting embodiments of the invention, the microwave imaging sensor is an ultra-wide band (UWB) microwave imaging sensor.

A device according to embodiments of the present invention can be used to monitor the condition of the RO membrane, i.e., the ability of the RO membrane to filter water by reverse osmosis; and to detect failures in the RO membrane and its environment, including, but not limited to: points of leakage of saline water through the RO membrane; saline super-saturation conditions; reduced fresh water transmission through the RO membrane; and fouling of the RO membrane by contaminants, such as biological or other organic material.

RO membrane failures can be detected by monitoring the dielectric constant of the fresh water region adjacent to the RO membrane. Because fresh water has a different dielectric constant from saline water, a failure point in the RO membrane can be detected immediately whenever a failure develops that leaks saline water into the output stream. The results of the monitoring can be used to determine in real time whether or not the RO membrane should be replaced.

Multiple reflected microwave signals from multiple antennas disposed around at least a portion of the RO membrane according to the geometric configuration of the RO membrane allow reconstruction of 3D images of the RO membrane and the regions of water between which the RO membrane forms a semi-permeable barrier. Comparison of images over time allows tracking changes in the performance of the RO membrane and projecting the time of optimum replacement.

Therefore, according to an embodiment of the present invention there is provided an apparatus for monitoring the condition of an in situ reverse osmosis membrane, wherein the reverse osmosis membrane forms a semi-permeable barrier between a region of water containing a dissolved salt and a region of water which is intended to be substantially free of the dissolved salt, the apparatus including: multiple microwave antennas disposed around at least a portion of the reverse osmosis membrane, wherein each microwave antenna is electrically connected to a transmit/receive circuit of multiple transmit/receive circuits; a bus electrically connecting the multiple transmit/receive circuits; and a processor/controller for reconstructing an image of the reverse osmosis membrane and the regions of water, to assess the condition of the reverse osmosis membrane.

BRIEF DESCRIPTION OF THE DRAWINGS

The subject matter disclosed may best be understood by reference to the following detailed description when read with the accompanying drawings in which.

Figure 1:
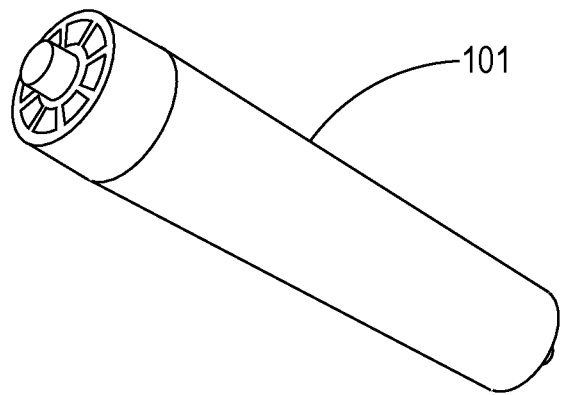
FIG. 1 illustrates a non-limiting example of a prior-art RO membrane unit.

For simplicity and clarity of illustration, water connections to RO membrane units for input and output streams are not shown in the drawings.

For addition simplicity and clarity of illustration, elements shown in the figures are not necessarily drawn to scale, and the dimensions of some elements may be exaggerated relative to other elements. In addition, reference numerals may be repeated among the figures to indicate corresponding or analogous elements.

DETAILED DESCRIPTION

FIG. 1 is a perspective view of a non-limiting prior-art RO membrane unit 101. In RO membrane unit 101, the RO membrane itself (not externally-visible) is coiled for compactness within a containing cartridge. Other configurations for RO membranes are also possible. RO membrane unit 101 is used herein as a non-limiting example of an RO membrane unit.

Figure 2:
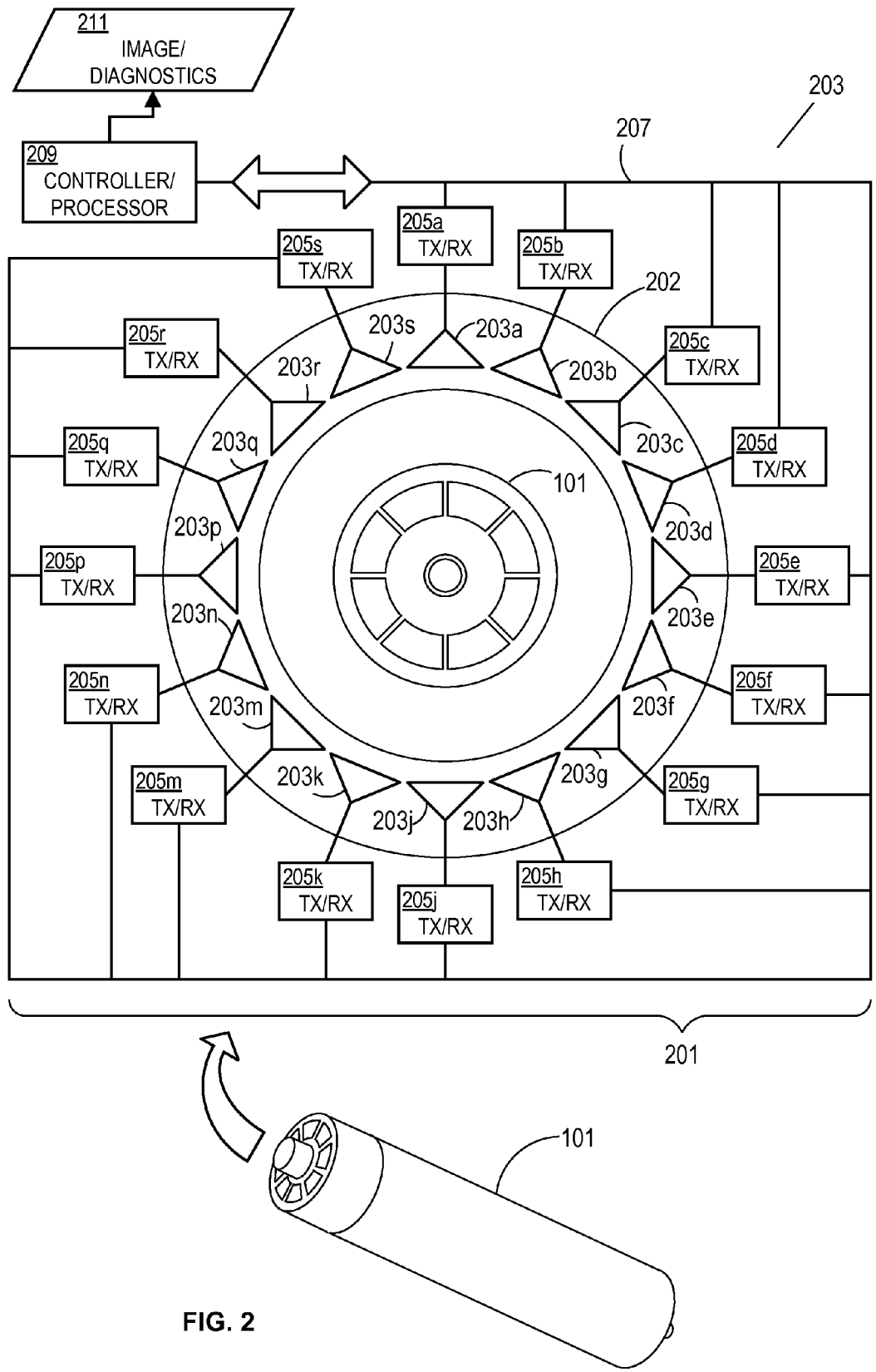
FIG. 2 illustrates an apparatus for monitoring RO membrane condition according to certain embodiments of the invention.

FIG. 2 is a cross section of an imaging apparatus 201 according to certain embodiments of the invention, which surrounds RO membrane unit 101, seen in an axial view. As noted previously, water connections to RO membrane unit 101 for input and output streams are not shown. However, it is understood that RO membrane unit 101 is installed and functioning, and that saline water and fresh water are present within RO membrane unit 101.

In an embodiment of the invention, apparatus 201 includes an antenna array 203 whose constituents include microwave antenna elements 203a, 203b, 203c, 203d, 203e, 203f, 203g, 203h, 203j, 203k, 203m, 203n, 203p, 203q, 203r, and 203s which are arranged around at least a portion of RO membrane unit 101. Transmit/receive (TX/RX) circuits 205a, 205b, 205c, 205d, 205e, 205f, 205g, 205h, 205j, 205k, 205m, 205n, 205p, 205q, 205r, and 205s are connected to respective elements, which in turn are connected via a bus 207 to a controller/processor 209, which analyzes the microwave signal reflections from RO membrane and the saline and fresh water therein, to produce a 3D image and diagnostics 211, by which the working condition of RO membrane unit 101 may be detected and assessed.

In an embodiment of the invention, apparatus 201 includes a supporting structure 202 to which antenna array 203 is affixed. In a related embodiment, supporting structure 202 is a printed circuit board and antenna elements 203a, 203b, 203c, 203d, 203e, 203f, 203g, 203h, 203j, 203k, 203m, 203n, 203p, 203q, 203r, and 203s are conventionally formed thereon. In another related embodiment, TX/RX circuits 205a, 205b, 205c, 205d, 205e, 205f, 205g, 205h, 205j, 205k, 205m, 205n, 205p, 205q, 205r, and 205s are integrated circuits attached to printed circuit board 202. In a further related embodiment, bus 207 is also formed on printed circuit board 202. In yet a still further related embodiment, controller/processor 209 is also attached to printed circuit board 202.

Figure 3:
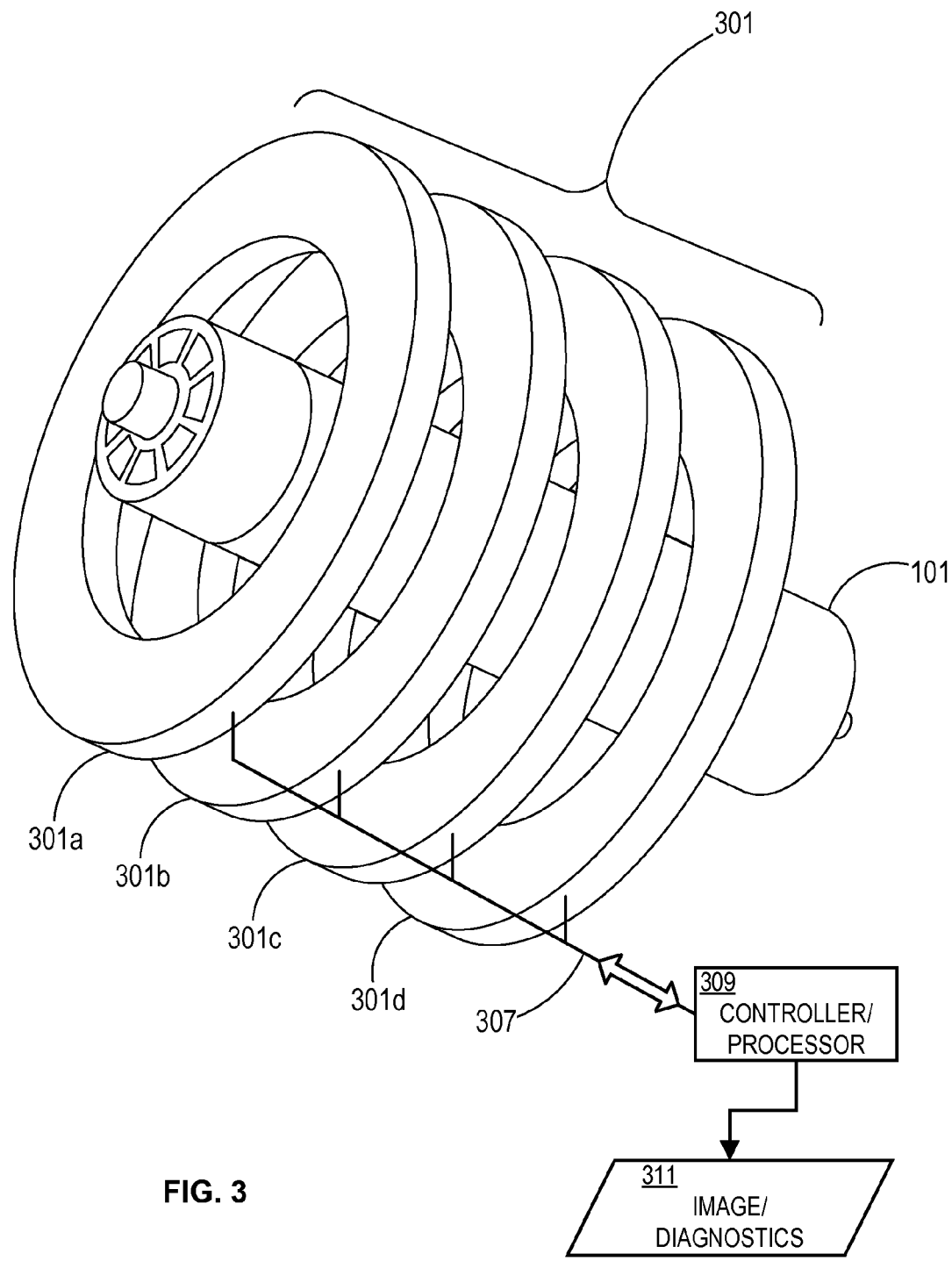
FIG. 3 illustrates an apparatus for monitoring RO membrane condition according to additional embodiments of the invention.

FIG. 3 illustrates an array 301 of antenna sub-arrays 301a, 301b, 301c, and 301d, according to certain embodiments of the invention. Array 301 extends imaging along the axis of RO membrane unit 101. In a related embodiment, a bus 307 connects a controller/processor 309 to the various sub-arrays of array 301. Controller/processor 309 analyzes the microwave signal reflections from RO membrane and the saline and fresh water therein, to produce a 3D image and diagnostics 311, by which the working condition of RO membrane unit 101 may be detected and assessed.

According to various embodiments of the invention, monitoring of RO membrane condition includes testing based on signal measurements of microwave radiation. In related embodiments, the signal measurements are manifest in images constructed from microwave radiation patterns. In certain embodiments, the relevant microwave signal measurements are of microwaves that are reflected by the RO membrane and/or water from the input and/or output streams; in other embodiments, the relevant microwave signal measurements pertain to the transmission of microwaves by the RO membrane and/or water from the input and/or output streams; in still other embodiments, the relevant microwave signal measurements pertain to the attenuation of microwaves by the RO membrane and/or water from the input and/or output streams. In certain embodiments of the invention, the characteristics of received microwave radiation are analyzed to determine a function of the dielectric constant of water in the input and/or output streams.

It is also understood that the above-disclosed embodiments are non-limiting and exemplary, and that different additional embodiments of the present invention have different geometrical arrangements, densities, numbers of antenna elements, and solid angle dispositions around the subject RO membrane.

What is claimed is:

1. An apparatus for monitoring the condition of an in situ reverse osmosis membrane, wherein the reverse osmosis membrane forms a semi-permeable barrier between a region of water containing a dissolved salt and a region of water which is intended to be substantially free of the dissolved salt, the apparatus comprising:
   a plurality of microwave antennas disposed around at least a portion of the reverse osmosis membrane, wherein each microwave antenna of the plurality is electrically connected to a transmit/receive circuit of a plurality of transmit/receive circuits;
   a bus electrically connecting the plurality of transmit/receive circuits; and
   a processor/controller for reconstructing an image of the reverse osmosis membrane and the regions of water, to assess the condition of the reverse osmosis membrane.

2. The apparatus of claim 1, wherein the condition of the reverse osmosis member is a change in the dielectric constant of the region of the water which is intended to be substantially free of the dissolved salt indicative of a failure of the reverse osmosis membrane.

* * * * *